United States Patent [19]

Duckenfield et al.

[11] Patent Number: 5,256,401
[45] Date of Patent: Oct. 26, 1993

[54] ANTIBACTERIAL ANTIPLAQUE MOUTHWASH COMPOSITION

[75] Inventors: Joan Duckenfield, North Brunswick; Lori VanMeter, Bridgewater; Shannon Campbell, Monmouth Junction; Nuran Nabi, N. Brunswick, all of N.J.

[73] Assignee: Colgate-Palmolive Company, Piscataway, N.J.

[21] Appl. No.: 899,412

[22] Filed: Jun. 16, 1992

Related U.S. Application Data

[63] Continuation-in-part of Ser. No. 398,592, Aug. 28, 1989, Pat. No. 5,188,821, which is a continuation-in-part of Ser. No. 291,712, Dec. 29, 1988, Pat. No. 4,894,220, which is a continuation-in-part of Ser. No. 8,901, Jan. 30, 1987, abandoned.

[51] Int. Cl.$^5$ .................................................. A61K 7/16
[52] U.S. Cl. ........................................ 424/49; 424/52
[58] Field of Search .................................... 424/49–58

[56] References Cited

U.S. PATENT DOCUMENTS

| | | | |
|---|---|---|---|
| 4,022,880 | 5/1977 | Vinson et al. | 424/49 |
| 4,562,064 | 12/1985 | Steltenkamp et al. | 424/49 |
| 4,894,220 | 1/1990 | Nabi et al. | 424/52 |
| 4,980,153 | 12/1990 | Jackson et al. | 424/52 |
| 5,015,466 | 5/1991 | Parran et al. | 424/52 |
| 5,015,467 | 5/1991 | Smitherman | 424/49 |
| 5,026,539 | 6/1991 | Jackson et al. | 424/49 |
| 5,032,385 | 7/1991 | Reed et al. | 424/49 |
| 5,037,635 | 8/1991 | Nabi et al. | 424/52 |
| 5,037,637 | 8/1991 | Gaffar et al. | 424/52 |
| 5,043,154 | 8/1991 | Gaffar et al. | 424/52 |
| 5,080,887 | 1/1992 | Gaffar et al. | 424/52 |
| 5,087,444 | 2/1992 | Jackson et al. | 424/49 |
| 5,096,699 | 3/1992 | Gaffar et al. | 424/49 |
| 5,096,701 | 3/1992 | White et al. | 424/52 |
| 5,112,600 | 5/1992 | Jackson et al. | 424/55 |
| 5,135,738 | 8/1992 | Gaffar et al. | 424/49 |
| 5,154,917 | 10/1992 | Ibrahim et al. | 424/7.1 |
| 5,156,835 | 10/1992 | Nabi et al. | 424/52 |
| 5,158,763 | 10/1992 | Gaffar et al. | 424/49 |
| 5,167,951 | 12/1992 | Gaffar et al. | 424/49 |
| 5,174,995 | 12/1992 | Davis | 424/400 |

FOREIGN PATENT DOCUMENTS

| | | |
|---|---|---|
| 161899 | 11/1985 | European Pat. Off. . |
| 251591 | 1/1988 | European Pat. Off. . |
| 271332 | 6/1988 | European Pat. Off. . |
| 278744 | 8/1988 | European Pat. Off. . |
| 161898 | 11/1989 | European Pat. Off. . |
| 420630 | 4/1991 | European Pat. Off. . |
| 3532860 | 3/1987 | Fed. Rep. of Germany . |
| 9200721 | 1/1992 | PCT Int'l Appl. . |
| 2200551 | 8/1988 | United Kingdom . |
| 2227661 | 8/1990 | United Kingdom . |

*Primary Examiner*—Shep K. Rose
*Attorney, Agent, or Firm*—Robert L. Stone; Murray M. Grill

[57] ABSTRACT

An oral composition mouthwash or liquid dentifrice containing an aqueous vehicle acceptable vehicle including an alcohol, a substantially water-insoluble noncationic antibacterial antiplaque agent, such as 2,4,4'-trichloro-21'-hydroxy-diphenyl ether (triclosan) wherein the antiplague agent is entirely dissolved in the solvent and the weight ratio of water to alcohol is in excess of about 10:1.

10 Claims, No Drawings

ANTIBACTERIAL ANTIPLAQUE MOUTHWASH COMPOSITION

This application is a continuation, of application Ser. No. 07/398,592, filed Aug. 28, 1989, now U.S. Pat. No. 5,188,821 which is a continuation-in-part of Ser. No. 07/291,712, filed Dec. 29, 1988, now U.S. Pat. No. 4,894,220, granted Jan. 16, 1990, which is a continuation-in-part of application Ser. No. 07/008,901, filed Jan. 30, 1987, now abandoned.

This invention relates to an antibacterial antiplaque mouthwash composition. More particularly, it relates to a mouthwash composition containing a substantially water-insoluble noncationic antibacterial agent effective to inhibit plaque.

Dental plaque is a soft deposit which forms on teeth as opposed to calculus which is a hard calcified deposit on teeth. Unlike calculus, plaque may form on any part of the tooth surface, particularly including at the gingival margin. Hence, besides being unsightly, it is implicated in the occurrence of gingivitis.

Accordingly, it is highly desirable to include antimicrobial agents which have been known to reduce plaque in oral compositions. Frequently, cationic antibacterial agents have been suggested.

Moreover, in U.S. Pat. No. 4,022,880 to Vinson et al, a compound providing zinc ions as an anticalculus agent is admixed with an antibacterial agent effective to retard the growth of plaque bacteria. A wide variety of antibacterial agents are described with the zinc compounds including cationic materials such as guanides and quaternary ammonium compounds as well as non-cationic compounds such as halogenated salicylanilides and halogenated hydroxydiphenyl ethers. The noncationic antibacterial antiplaque halogenated hydroxydiphenyl ether, triclosan, has also been described in combinations with zinc citrate trihydrate in European Patent 0161,899 to Saxton et al. Also, in European Patent Publication 0271,332 to Davis, mouthwash propylene glycol which also contains triclosan is disclosed and in PCT Publication No. WO92/00721 to Reed, mouthwash with a broad range of ethanol content which also contains triclosan is disclosed.

The cationic antibacterial materials such as chlorhexidine, benzthonium chloride and cetyl pyridinium chloride have been the subject of great investigation as antibacterial antiplaque agents. However, they are generally not effective when used with anionic materials. Noncationic antibacterial materials, on the other hand, can be compatible with anionic components in an oral composition.

However, oral compositions typically are mixtures of numerous components and even such typically neutral materials as humectants can affect performance of such compositions.

Moreover, even noncationic antibacterial antiplaque agents may have limited antiplaque effectiveness with commonly employed materials such as polyphosphate anticalculus agents which are disclosed together to U.S. Pat. No. 4,894,220 of Nabi et al, in British Patent Publication 2,200,551 of Gaffar et al and EP 0251,591 of Jackson et al. In British Patent Publication 2,235,133 of Gaffar et al, it is shown that the antiplaque effectiveness is greatly enhanced by including an antibacterial-enhancing agent (AEA) which enhances the delivery of said antibacterial agent to, and retention thereof on, oral surfaces and by providing optimized amounts and ratios of polyphosphate and AEA.

Further, even when polyphosphate anticalculus agent is not present as shown in U.S. Pat. No. 4,894,220 (noted above) and in British Patent Publication 2,227,660 Gaffar et al, antiplaque effectiveness on soft oral tissue is optimized in oral compositions containing the noncationic antibacterial agent and said AEA.

It is an advantage of this invention that a mouthwash composition is obtained in which substantially water-insoluble noncationic antibacterial agent is solubilized without excessive presence of solvent to provide substantial antiplague effectiveness.

It is an advantage of this invention that substantial antiplaque effectiveness is attained even when the said AEA is not present.

It is an advantage of the invention that by limiting the amount of solvent for the antibacterial agent while achieving its complete solubilization in the mouthrinse, possible side-effects of the solvent, such as a "burning" sensation provided by alcohol, are reduced.

it is an advantage of this invention that the antiplaque mouthwash is effective when used before or after toothbrushing.

Additional advantages of this invention will be apparent from consideration of the following specification.

In accordance with certain of its aspects, this invention relates to a mouthwash composition having a vehicle comprising water and an aqueous nontoxic alkyl mono-or di-hydric alcohol and dissolved therein an effective antiplaque amount up to about 0.09%. of a substantially water insoluble noncationic antibacterial agent, said alcohol being a solvent for said antibacterial agent, wherein the weight ratio of water to alcohol is in excess of about 10:1 and the amount of solvent is sufficient to completely dissolve said antibacterial agent in said mouthwash composition.

Typical examples of water insoluble noncationic antibacterial agents which are particularly desirable for their antiplaque effectiveness, safety and formulation are:

Halogenated Diphenyl Ethers

2',4,4'-trichloro-21'-hydroxy-diphenyl ether (Triclosan)
2,2'-dihydroxy-5,5'-dibromo-diphenyl ether

Halogenated Salicylanilides

4', 5'-dibromosalicylanilide
3,4'5'-trichlorosalcylanilide
3,4,5-tribromosalicylanilide
2,3,3',5-tetrachlorosalicylanilide
3,3,3',5-tetrachlorosalicylanilide
3,5-dibromo-3'-trifluoromethyl salicylanilide
5-n-octanoyl-3'-trifluoromethyJ. salicylanilide
3,5-dibromo-4'trifluoromethyl salicylanilide
3,5-dibromo-3'-trifluoromethyl salicylanilide (Flurophene)

Benzoic Esters

| | |
|---|---|
| Methyl | - p-Hydroxybenzoic Ester |
| Ethyl | - p-Hydroxybenzoic Ester |
| Propyl | - p-Hydroxybenzoic Ester |
| Butyl | - p-Hydroxybenzoic Ester |

Sesquiterpene Alcohols

Farnesol

Nerolidol
Bisabolol
Santalol

Halogenated Carbanilides 3,4,4'-trichlorocarbanilide
3-trifluoromethyl-4,4'-dichlorocarbanilide
3,3,4'-trichlorocarbanilide Phenolic Compounds (including phenol and its homologs, mono-and poly-alkyl and aromatic halo (e.g.,Cl, Br, I)-phenols, resorcinol and catechol and their derivatives and bisphenolic compounds). Such compounds include inter alia:

Phenol and its Homologs

| Phenol | |
|---|---|
| 2-Methyl | - Phenol |
| 3-Methyl | - Phenol |
| 4-Methyl | - Phenol |
| 4-Ethyl | - Phenol |
| 2,4-Dimethyl | - Phenol |
| 2,5-Dimethyl | - Phenol |
| 3,4-Dimethyl | - Phenol |
| 2,6-Dimethyl | - Phenol |
| 4-n-Propyl | - Phenol |
| 4-n-Butyl | - Phenol |
| 4-n-Amyl | - Phenol |
| 4-tert-Amyl | - Phenol |
| 4-n-Hexyl | - Phenol |
| 4-n-Heptyl | - Phenol |
| 2-Methoxy-(2-Propenyl)-Phenol (Eugenol) | |
| 2-Isopropyl-5-Methyl-Phenol (Thymol) | |

Mono- and Poly-Alkyl and Aromatic Halophenols

| Methyl | - p-Chlorophenol |
|---|---|
| Ethyl | - p-Chlorophenol |
| n-Propyl | - p-Chlorophenol |
| n-Butyl | - p-Chlorophenol |
| n-Amyl | - p-Chlorophenol |
| n-Hexyl | - p-Chlorophenol |
| Cyclohexyl | - p-Chlorophenol |
| n-Heptyl | - p-Chlorophenol |
| n-Octyl | - p-Chlorophenol |
| O-Chlorophenol | |
| Methyl | - o-Chlorophenol |
| Ethyl | - o-Chlorophenol |
| n-Propyl | - o-Chlorophenol |
| n-Butyl | - o-Chlorophenol |
| n-Amyl | - o-Chlorophenol |
| Tert-Amyl | - o-Chlorophenol |
| n-Hexyl | - o-Chlorophenol |
| n-Heptyl | - o-Chlorophenol |
| p-Chlorophenol | |
| o-Benzyl | - p-Chlorophenol |
| o-Benzyl-m-methyl | - p-Chlorophenol |
| o-Benzyl-m-methyl | - p-Chlorophenol |
| o-Phenylethyl | - p-Chlorophenol |
| o-Phenylethyl-m-methyl | - p-Chlorophenol |
| 3-Methyl | - p-Chlorophenol |
| 3,5-Dimethyl | - p-Chlorophenol |
| 6-Ethyl-3-methyl | - p-Chlorophenol |
| 6-n-Propyl-3-methyl | - p-Chlorophenol |
| 6-iso-Propyl-3-methyl | - p-Chlorophenol |
| 2-Ethyl-3,5-dimethyl | - p-Chlorophenol |
| 6-sec Butyl-3-methyl | - p-Chlorophenol |
| 2-iso-Propyl-3-5-methyl | - p-Chlorophenol |
| 6-Diethylmethyl-3-methyl | - p-Chlorophenol |
| 6-iso-Propyl-2-ethyl-3-methyl | - p-Chlorophenol |
| 2-sec amyl-3,5-dimethyl | - p-Chlorophenol |
| 2-Diethylmethyl-3,5-dimethyl | - p-Chlorophenol |
| 6-sec Octyl-3-methyl | - p-Chlorophenol |
| p-Bromophenol | |
| Methyl | - p-Bromophenol |
| Ethyl | - p-Bromophenol |
| n-Propyl | - p-Bromophenol |
| n-Butyl | - p-Bromophenol |
| n-Amyl | - p-Bromophenol |
| sec-Amyl | - p-Bromophenol |
| n-Hexyl | - p-Bromophenol |
| Cyclohexyl | - p-Bromophenol |
| o-Bromophenol | |
| Tert-Amyl | - o-Bromophenol |
| n-Hexyl | - o-Bromophenol |
| n-Propyl-m,m-Dimethyl | - o-Bromophenol |
| 2-Phenyl Phenol | |
| 4-chloro-2-methyl phenol | |
| 4-chloro-3-methyl phenol | |
| 4-chloro-3,5-dimethyl phenol | |
| 2,4-dichloro-3,5-dimethylphenol | |
| 3,4,5,6-terabromo-2-methylphenol | |
| 5-methyl-2-pentylphenol | |
| 4-isopropyl-3-methylphenol | |
| 5-chloro-2-hydroxydiphenylmethane | |

Resorcinol and Its Derivatives

| Resorcinol | |
|---|---|
| Methyl | - Resorcinol |
| Ethyl | - Resorcinol |
| n-Propyl | - Resorcinol |
| n-Butyl | - Resorcinol |
| n-Amyl | - Resorcinol |
| n-Hexyl | - Resorcinol |
| n-Heptyl | - Resorcinol |
| n-Octyl | - Resorcinol |
| n-Nonyl | - Resorcinol |
| Phenyl | - Resorcinol |
| Benzyl | - Resorcinol |
| Phenylethyl | - Resorcinol |
| Phenylpropyl | - Resorcinol |
| p-Chlorobenzyl | - Resorcinol |
| 5-Chloro | -2,4-Dihydroxydiphenyl Methane |
| 4'-Chloro | -2,4-Dihydroxydiphenyl Methane |
| 5-Bromo | -2,4-Dihydroxydiphenyl Methane |
| 4'-Bromo | -2,4-Dihydroxydiphenyl Methane |

Bisphenolic Compounds 2,2'-methylene bis (4-chlorophenol)
2,2'-methylene bis (3,4,6-trichlorophenol)
2,2'-methylene bis (4-chloro-6-bromophenol)
bis (2-hydroxy-3,5-dichlorophenyl) sulfide
bis (2-hydroxy-5-chlorobenzyl) sulfide The noncationic antibacterial agent is present in the mouthwash composition of the present invention in an effective antiplaque amount up to about 0.09%, typically about 0.01–0.09% by weight, preferably about 0.03–0.06%. The antibacterial agent is substantially water-insoluble, meaning that its solubility is less than about 1% by weight in water at 25° C. and even may be substantially non-existent. Thus, water is not a solvent even when the antibacterial agent is present in an amount such as 0.01%.

The preferred halogenated diphenyl ether is triclosan. The preferred phenolic compounds are phenol, thymol, eugenol, and 2,2'methylene bis(4-chloro-6-bromophenol). The preferred sesquiterpene alcohols are nerolidol and bisabolol.

Triclosan is disclosed in aforementioned U.S. Pat. No. 4,022,880 as an antibacterial agent in combination with an anticalculus agent which provides zinc ions and in German Patent Disclosure 3,532,860 in combination with a copper compound. In European Patent Disclosure 0278,744 it is disclosed in combination with a tooth desensitizing agent containing a source of potassium ion. It is also disclosed as an antiplaque agent in a dentifrice formulated to contain a lamellar liquid crystal surfactant phase having a lamellar spacing of less than 6.0 mn and which may optionally contain a zinc salt in published European Patent Application 0161898 of Lane et al and in a dentifrice containing zinc citrate trihydrate in published European Patent Disclosure 0161899 to Saxton et al. Other patent disclosures of triclosan oral compositions are set forth earlier. Sesquiterpene alcohol oral compositions are described in European Patent Disclosure 0420,630 to Robinson et al, In the present invention, the oral composition is a mouthwash and is substantially liquid in character. In such composition the vehicle comprises a water-alcohol mixture, with the weight ratio of water to alcohol being in excess of 10:1, generally up to about 20:1, preferably about 10.5:1 to about 18:1 and more preferably about 12:1 to about 16:1. The total amount of water-alcohol mixture in this type of preparation is typically in the range of from about 70 to about 99.9% by weight. The alcohol is a non-toxic alkyl mono- or di-hydric alcohol such as ethanol, n-propanol, isopropanol or propylene glycol. Humectant such as glycerine, sorbitol or xylitol or mixtures thereof, may be present in amount of about 10–20% by weight. Reference herein to sorbitol refers to the material typically as available commercially in 70% aqueous solution. The humectants do not appear to be solvents for the antibacterial agent. In addition to the alcohol, solvents for the antibacterial agent which may be present particularly include surface active agent and flavor oil. Ethanol is the preferred non-toxic alcohol. The alcohol dissolves the water-insoluble non-cationic antibacterial agent, or if flavoring oil and/or surface-active agent is present, assists in the solvent action.

In other words, as indicated, the noncationic antibacterial agent is substantially water-insoluble. However, in the mouthwash of the present invention, organic surface-active agent, flavoring oil and, particularly, non-toxic alcohol act as solvents which are believed to aid dissolving the antibacterial agent so that it can reach soft oral tissue at or near the gums as well as tooth surfaces. The noncationic antibacterial agent is entirely dissolved in the mouthwash. Preferably the amount of alcohol does not exceed about 40% by weight over the amount required to completely dissolve the antibacterial agent and most preferably does not exceed about 209 by weight over the amount needed to completely dissolve the antibacterial agent in the mouthwash composition. Thus, in an aqueous mouthrinse containing 0.03% by weight of triclosan, minor amounts of organic surface-active agent and flavoring oil and ethanol, it would require about 5% by weight of ethanol to fully dissolve the triclosan, and most preferably, the amount of ethanol would be between 5% and about 7% by weight, with the weight ratio of water to ethanol being in excess of about 10:1. In this manner, it is possible to achieve optimum antiplaque effectiveness even if an antibacterial enhancing agent (AEA) is not present to assist delivery of the antibacterial agent and its retention at gum and tooth surfaces.

Organic surface-active agents are also desirably used in the compositions of the present invention to achieve increased prophylactic action, assist in achieving thorough and complete solvent dispersion of the antiplaque antibacterial agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, higher fatty acid esters of taurine and the substantially saturated higher aliphatic acyl amides of lower aliphatic amino carboxylic acid compounds, such as those having 12 to 16 carbons in the fatty acid, alkyl or acyl radicals, and the like. Examples of the last mentioned taurines and amides are N-methyl-N-cococyl taurate, N-methyl-N-oleoyl taurate, N-methyl-N-palmitoyl-taurate, N-lauroyl sarcosinate, and the sodium, potassium, and ethanolamine salts of N-lauroyl, N-myristoyl, or N-palmitoyl sarcosine which should be substantially free from soap or similar higher fatty acid material. The taurine compounds particularly assist solution. The use of the sarconsinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Surface active agent, including mixtures thereof, is typically present in amount of about 0.4–5% by weight, preferably about 0.4–0.6% for anionic agents and about 1–2.5% for non-ionic agents.

Although ethylene glycol can be a solvent, it is preferred that it not be the solvent alcohol. Significant amounts of polyethylene glycol particularly of molecular weight of 600 or more should be avoided since polyethylene glycol effectively inhibits the antibacterial activity of the noncationic antibacterial agent. For instance, polyethylene glycol (PEG) 600 when present with triclosan in a weight ratio of 25 triclosan:1 PEG 600 reduces the antibacterial activity of triclosan by a factor of about 16 from that prevailing in the absence of the polyethylene glycol.

Any suitable flavoring oil and/or sweetening material may also be employed. As indicated above, the flavoring oil is believed to assist as a solvent for the antibacterial agent. Examples of suitable flavoring oils are e.g. oil of spearmint, peppermint, winter green, sassafras, clove, sage, eucalyptus, marjoram, cinnamon, lemon, and orange. Suitable sweetening agents include sucrose, lactose, maltose, xylitol, sodium cyclamate, perillartine, AMP (aspartyl phenyl alanine, methyl ester), sodium saccharine and the like. Suitably, flavoring oil may comprise from about 0.04% to 5% typically about 0.08–2.5%, preferably about 0.08–0.15% by weight. Sweetener may comprise about 0.005–2.5%, preferably about 0.005–0.01% for sodium saccharine and about 1–2.5% for sodium cyclamate.

Patent disclosures referred to above describe antibacterial-enhancing agent (AEA) to enhance delivery of antibacterial agent to and retention on oral surfaces. A particular improvement of the present invention is that AEA is not required when the water-alcohol ratio and solvent concentrations are observed. However, the AEA may be optionally employed in amounts of up to about 4% or more, such as about 0.05% to about 4%, preferably about 0.1% to about 3%, more preferably about 0.5% to about 2.5% by weight.

This AEA may be a simple compound, preferably a polymerizable monomer, more preferably a polymer, which latter term is entirely generic, including for example oligomers, homopolymers, copolymers of two or more monomers, ionomers, block copolymers, graft copolymers, cross-linked polymers and copolymers, and the like. The AEA may be natural or synthetic, and water insoluble or preferably water (saliva) soluble or swellable (hydrotable, hydrogel forming). it has an average molecular weight of about 100 to about 1,000,000, preferably about 1,000 to about 1,000,000, more preferably about 2,000 or 2,500 to about 250,000 or 500,000.

The AEA ordinarily contains at least one delivery-enhancing group, which is preferably acidic such as sulfonic, phosphinic, or more preferably phosphonic or carboxylic, or salt thereof, e.g. alkali metal or ammonium, and at least one organic retention-enhancing group, preferably a plurality of both the delivery-enhancing and retention-enhancing groups, which latter groups preferably have the formula—(X)n-R wherein X is O, N, S, SO, $SO_2$, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives", are intended to include substituents of R which are generally non-hydrophilic and do not significantly interfere with the desired functions of the AEA as enhancing the delivery of the antibacterial agent to, and retention thereof on, oral surfaces such as halo, e.g. Cl, Br and I and the like. The polycarboxylate methyl vinyl ether/maleic anhydride copolymer, for instance, available as Gantrez is preferred. Further description of AEA is set forth in British Patent Publication 2,227,660, which is incorporated herein by reference.

The AEA can provide a thickening quality to increase the viscosity of the mouthwash. Such increase in viscosity may also be achieved by employing a minor amount, such as about 0.01–0.1% by weight, preferably about 0.02–0.06% of a thickener, such as xanthan.

The mouthwash desirably may also contain sodium benzoate which has been described as an antiplaque agent in U.S. Pat. No. 4,657,758 of Goldenberg et al and is also known as a preservative. It is typically present in amount of about 0.05–1% by weight, preferably about 0.1–0.8%.

Sodium bicarbonate which is disclosed in U.S. Pat. No. 4,132,770 of Barth as an additive to mouthwash to stimulate and refresh taste also may be desirably included in mouthwash of the present invention in amount of about 0.05–10% by weight, preferably about 0.1–1%.

Allantoin, aluminum dihydroxy allantoinate and aluminum chlorohydroxy-allantoinate are disclosed in U.S. Pat. No. 3,928,555 of Gault as agents to promote healing of sensitive oral tissue. Such agent may also be desirably employed in mouthwash of the present invention. A desirable range is about 0.1–1% by weight, preferably about 0.1–0.5%.

When sodium benzoate, sodium bicarbonate and allantoin are present the mouthwash is most preferably introduced into the oral cavity before toothbrushing.

The oral mouthwash composition may also contain an anticaries amount of fluoride ion source sufficient to supply about 25 ppm. to 5,000 ppm. of fluoride ions. The sources of fluoride ions, or fluorine-providing component are well known in the art as anticaries agents. These compounds may be slightly soluble in water or more preferably fully water-soluble. They are characterized by ability to release fluoride ions in water and by substantial freedom from undesired reaction with other compounds of the oral preparation. Among these materials are inorganic fluoride salts, such as soluble alkali metal fluorides, for example, sodium fluoride, potassium fluoride and ammonium fluoride, as well as a copper fluoride such as cuprous fluoride, zinc fluoride, barium fluoride, sodium fluorosilicate, ammonium fluorosilicate, sodium fluorozirconate, ammonium fluorozirconate, sodium monofluorophosphate, aluminum monoand di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a non-toxic amount, generally about 0.0005% to about 3.0% in the preparation. In a mouthwash preparation, an amount of such compound which releases up to about 5,000 ppm of F ion by weight of be preparation is considered satisfactory. Any suitable effective anticaries minimum amount of such compound may be used, but it is preferable to employ sufficient compound to release about 100 to 2,000 ppm., more preferably about 100 or 300 to about 1,500 ppm of fluoride ion.

Typically, in the cases of alkali metal fluorides, this component is present in an amount up to about 2% by weight, based on the weight of the preparation, and preferably in the range of about 0.02% to 1%. In the case of sodium monofluorophosphate, the compound is preferably present in an amount of about 0.075–3%.

Various other materials may be incorporated in the oral preparations of this invention such as azacycloalkane diphosphonates (e.g. azacycloheptane diphosphonate compound), sodium salicylate, whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which could complex with AEA with active components of the instant invention are to be avoided, particularly if AEA is present.

It will be understood that, as is conventional, the oral preparations are to be sold or otherwise distributed in suitable labelled packages. This a jar of mouthrinse will be a label describing it, in substance, as a mouthrinse or mouthwash and having directions for its use.

In the preferred practice of this invention an oral composition according to this invention such as a mouthwash containing a composition of the present invention is preferably applied regularly to dental enamel and oral tissue such as every day or every second or third day or preferably from 1 to 3 times daily, at a pH of about 4 to 8, generally about 6 to 8, for at least 2 weeks up to 8 weeks or more up to lifetime. The mouthwash is desirably used after toothbrushing or before toothbrushing.

The following examples are further illustrative of the nature of the present invention, but it is understood that the invention is not limited thereto, all amounts and proportions referred to herein and in the appended claims are by weight, unless otherwise indicated.

EXAMPLE 1

Differences in Triclosan delivery from mouthrinse vehicles which differ in solubilization capacity is illustrated by the following experiments:

The Saliva Coated Hydroxy Apatite Uptake Test (SCHAP test) is an in vitro test model which mimics delivery of nonionic antimicrobials to oral surfaces. In this test, saliva coated Hydroxyapatite (HAP) disks are a model for pellicle coated teeth. They are incubated with mouthrinses for a set period of time (0.5 hour), rinsed and then the Triclosan adsorbed onto the disks is extracted and analyzed by high pressure liquid chromatography (HPLC).

This test was used to compare prototype Triclosan rinse formulations with the following variables:
(1) Humectants:
 A. 5% glycerine/3.5% sorbitol
 B. 10% lot glycerine/7% sorbitol
 C. 5% glycerine/14% sorbitol
 D. 20% glycerine/3.5% sorbitol
 E. 20% glycerine/14% sorbitol
(2) Solvents:
 F. 5% ethanol/0% propylene glycol
 G. 5% ethanol/7% propylene glycol
 H. 15% ethanol/0% propylene glycol
 I. 10% ethanol/7% propylene glycol
 J. 15% ethanol/7% propylene glycol The results of SCHAP tests are analyzed by Taguchi Analysis (as described in Genichi Taguchi: Experimental Designs, 3rd Edition (Volumes 142), Maruzan 1976, 1977, and Genichi Taguchi, Yuin Wu; Off-Line Quality Control Central Japan Quality Control Association, 1980) to determine individual component relationships to Triclosan uptake with the following results which demonstrate that lowering humectant and ethanol concentrations (and, therefore, increasing water concentration) increases uptake of antiplaque agent onto saliva coated HAP disks, thereby indicating increased retention of the antiplaque agent on oral tissues.

| Component | Triclosan Uptake (ug/disk) | % Increase in Uptake |
|---|---|---|
| 15% Ethanol | 17.82 | — |
| 5% Ethanol | 22.67 | 27.2 |
| 7% Propylene glycol | 17.64 | — |
| 0% Propylene glycol | 22.86 | 29.6 |
| 20% Glycerine | 16.60 | — |
| 5% Glycerine | 23.90 | 44.0 |
| 14% Sorbitol | 18.35 | — |
| 3.5% Sorbitol | 22.15 | 20.7 | in a second SCHAP test, two Triclosan rinse formulations differing in humectant, solvent and water concentration are compared:
(1) Rinse A (Low Water/High Solvent):
 Humectants: 10% glycerine, 7% sorbitol
 Solvents: 10% ethanol, 7% propylene glycol
 Water: 65.05%
 Polysorbate 20 0.1%
 Triclosan: 0.03%
(2) Rinse B (High water/Low Solvent Level Sufficient to dissolve all Triclosan):
 Humectanbs: 15% glycerine
 Solvents: 6% ethanol
 Water: 77.41%
 Polysorbate 20 0.1%
 Triclosan: 0.03%

The results of the SCHAP test are as follows:

| Rinse | Triclosan Uptake (ug/disk) | % Increase in Uptake |
|---|---|---|
| Rinse A | 35.03 ± 0.77 | — |
| Rinse B | 42.51 ± 2.09* | 21.4 |

*Statistically significant difference (p = 0.05) vs Rinse A.

In a third SCHAP test, two similar Triclosan formulations but without polysorbate, are compared:
(1) Rinse A (Low Water/High Solvent)
 Humectants: 10% glycerine, 7% sorbitol
 Solvents: 10% ethanol, 7% propylene glycol
 Water: 65.05%
 Triclosan: 0. 03%
(2) Rinse C (High Water/Low Solvent Sufficient to dissolve all Triclosan)
 Humectants: 15% glycerine
 Solvents: 6% ethanol
 Water: 77.85%
 Triclosan: 0.03%

The results of the SCHAP test are as follows:

| Rinse | Triclosan Uptake (ug/disk) | % Increase in Uptake |
|---|---|---|
| Rinse A | 28.56 ± 2.20 | — |
| Rinse C | 47.53 ± 2.50 | 66.4 |

*Statistically significant difference (p = 0.05) vs Rinse A.

In a fourth SCHAP test, Triclosan formulations varying only in ethanol concentration are compared:
Rinse Ethanol Concentrations
 3% Ethanol
 6% Ethanol
 7.5% Ethanol
 12% Ethanol The results of the SCHAP are as follows:

| Ethanol Concentration | Triclosan Uptake (ug/disk) | % Increase in Uptake |
|---|---|---|
| 12% Ethanol | 37.93 ± 1.58 | — |
| 7.5% Ethanol | 41.76 ± 3.38 | 10.1 |
| 6% Ethanol | 45.94 ± 1.11* | 21.1 |
| 3% Ethanol | 46.09 ± 2.79* | 21.5 |

*Statistically significant difference (p = 0.05) vs 12% Ethanol.

It is noteworthy that increased uptake can also be obtained even with ethanol completely absent. However, the mouthrinse does not remain clear.

The above results indicate the following optimal ratios and deviations therefrom:
Triclosan/Kumectant ratio of 0.03/15 or 1/500 or lower.
Triclosan/Solvent ratio of 0.03/6 or 1/200 or lower.
Triclosan/Water ratio of 0.03/78 or 1/2600 or higher,
When these parameters are observed the weight ratio of water to solvent exceeds about 10:1, triclosan is completly dissolved and the amount of ethanol is at least that required to completely dissolve Triclosan in the formula, without a very large excess.

EXAMPLE 2

The following formula is an effective antiplaque mouthwash when applied to the oral cavity including teeth and gums after brushing:

| INGREDIENTS | PARTS |
|---|---|
| Ethyl Alcohol | 5.000 |
| Flavor | 0.500 |
| Triclosan | 0.030 |
| Sodium methyl Cocoyl Taurate (95%) | 0.450 |
| Sorbitol (70%) | 20.000 |
| Glycerine | 5.000 |
| Polyvinyl Methyl Ether/Maleic Anhydride Gantrez S-97 | 1.920 |
| Sodium Hydroxide | 0.120 |
| Sodium Fluoride | 0.025 |
| Color (0.1% solution) | 0.300 |
| Water | 67.250 |

Any of phenol, thymol, eugenol and 2,21' methylene bis (4-chloro-6-bromophenol) can effectively replace triclosan and any of n-propanol, isopropanol and propylene glycol can effectively replace ethanol at the amount sufficient to completely dissolve the plaque inhibiting agent.

EXAMPLE 3

The following formulas are effective mouthwashes when applied to the oral cavity including teeth and gums before or after brushing.

| Ingredients | Parts A | Parts B |
|---|---|---|
| Deionized Water | 77.952 | 77.732 |
| Glycerine | 15.000 | 15.000 |
| Ethanol 95% | 6.000 | 6.000 |
| Sodium Methyl cocoyl Taurate | 0.250 | 0.250 |
| Sodium lauryl sulfate | 0.200 | 0.200 |
| Allantoin | 0.200 | 0.200 |
| Flavor | 0.100 | 0.100 |
| Sodium benzoate | 0.100 | 0.100 |
| Sodium salicylate | 0.100 | 0.100 |
| Triclosan | 0.030 | 0.030 |
| Xanthan gum | 0.030 | — |
| Sodium fluoride | 0.025 | 0.025 |
| FD & C Red #40 Color | 0.008 | 0.008 |
| Sodium saccharin | 0.005 | 0.005 |
| Methyl vinyl ether - Maleic Anhydride Copolymer - Gantrez S-97 | — | 0.250 |

Any of phenol, thymol, eugenol and 2,2'methylene bis (4-chloro-6-bromophenol) can be effectively substituted for triclosan.

Any of ethanol n-propanol, is propanol and propylene glycol can be effectively substituted for triclosan.

EXAMPLE 4

The following formulas are effective antiplaque mouthwashes when applied before or after toothbrushing:

| Ingredients | Parts A | B | C |
|---|---|---|---|
| 95% Ethanol Alcohol | 6.000 | 6.000 | 6.000 |
| Flavor | 0.157 | 0.080 | 0.157 |
| Triclosan | 0.030 | 0.030 | 0.030 |
| 99% Glycerine | 15.000 | 15.000 | 15.000 |
| Sodium methyl cocoyl Taurate (95%) | 0.250 | 0.250 | 0.250 |
| Polyoxyethylene-Polyoxypropylene Block Copolymer Pluronic F-127 | — | — | 2.000 |
| Sodium Lauryl Sulfate Powder | 0.200 | 0.200 | 0.200 |
| Allantoin | 0.200 | 0.200 | 0.200 |
| Sodium Benzoate | 0.100 | 0.100 | 0.100 |
| Sodium Bicarbonate (Extra fine) | 0.100 | 0.100 | 0.100 |
| Sodium Salicylate | 0.100 | 0.100 | 0.100 |
| Sodium Saccharin | 0.010 | 0.010 | 0.010 |
| Xanthan Gum | 0.030 | 0.030 | 0.030 |
| Sodium Fluoride | — | — | 0.025 |
| Color | 0.007 | 0.007 | 0.007 |
| Water | 77.816 | 77.893 | 76.011 |

Any of phenol, thymol. eugenol and 2,2'-methylene bis (4-chloro-6-broznophenol) as effectively replace triclosan and any of n-propanol, isopropanol and propylene glycol can effectively replace ethanol at the amount sufficient to completely dissolve the plaque inhibiting agent.

EXAMPLE 5

The following pleasant tasting effective antiplaque mouthwash is prepared:

| Ingredients | Parts |
|---|---|
| 95% Ethyl Alcohol | 6.000 |
| Flavor | 0.160 |
| Nerolidol | 0.040 |
| Bisabolol | 0.010 |
| 99% Glycerine | 10.000 |
| Sodium methyl cocoyl Taurate (95%) | 0.250 |
| Polyoxyethylene-Polyoxypropylene Block Copolymer Pluronic F-127 | 0.050 |
| Sodium Lauryl Sulfate Powder | 0.200 |
| Sodium Saccharin | 0.020 |
| Xanthan Gum | 0.030 |
| Sodium Fluoride | 0.025 |
| Benzoic acid | 0.015 |
| Water | 73.155 |

This invention has been described with respect to certain preferred embodiments and it will be understood that modifications and variations thereof obvious to those skilled in the art are to be included within the purview of this application and the scope of the appended claims.

We claim:

1. A mouthwash composition having a vehicle comprising water and an aqueous nontoxic alkyl mono-or di-hydric alcohol and dissolved therein an effective antiplaque amount up of about 0.01 to about 0.09% of a substantially water insoluble noncationic antibacterial agent, said alcohol being a solvent for said antibacterial agent, wherein the weight amount ratio of water to alcohol is at least 10:1 and the amount of solvent is sufficient to completely dissolve the amount of said antibacterial agent in said mouthwash composition.

2. The mouthwash claimed in claim 1 wherein said antiplaque amount is about 0.03–0.06% by weight.

3. The mouthwash claimed in claim 2 wherein said weight ratio of water to alcohol is from about 10:1 to about 20:1.

4. The mouthwash claimed in claim 3 wherein said weight ratio is from about 12:1 to about 16:1.

5. The mouthwash claimed in claim 1 wherein said alcohol is ethanol.

6. The mouthwash claimed in any one of claims 1 or 2 to 5 wherein said antibacterial agent is triclosan.

7. The mouthwash claimed in any one of claims 1 or 2 to 5 wherein said antibacterial agent is nerolidol.

8. The mouthwash claimed in any one of claims 1 or 2 to 5 wherein an antibacterial enhancing agent containing a delivery group and an organic retention enhancing group is present in amount of about 0.05-7% by weight.

9. The mouthwash claimed in claim 8 where said antibacterial enhancing group is a polycarboxylate.

10. The mouthwash claimed in claim 3 wherein said antibacterial agent is triclosan present in amount of about 0.03% by weight.

* * * * *